United States Patent [19]

Muzzammel

[11] Patent Number: 5,997,506
[45] Date of Patent: Dec. 7, 1999

[54] HYSTEROSONOGRAM/ HYSTEROSALPINGOGRAM CANNULA WITH SOFT SEAL

[76] Inventor: Mohiuddin M. Muzzammel, 11323 Bright Pond La., Reston, Va. 20194

[21] Appl. No.: 09/220,066

[22] Filed: Dec. 23, 1998

Related U.S. Application Data

[60] Provisional application No. 60/080,469, Apr. 2, 1998.

[51] Int. Cl.⁶ .................................................. A61M 29/00
[52] U.S. Cl. .......................... 604/104; 604/523; 604/264
[58] Field of Search ............................... 604/27, 93, 104, 604/264, 278, 279, 523, 539, 275

[56] References Cited

U.S. PATENT DOCUMENTS

| | | | |
|---|---|---|---|
| 85,995 | 1/1869 | Buffon . | |
| 2,610,627 | 9/1952 | Watt et al. | 128/239 |
| 3,385,300 | 5/1968 | Holter | 128/348 |
| 3,721,229 | 3/1973 | Panzer | 128/2 |
| 3,796,211 | 3/1974 | Kohl . | |
| 3,970,090 | 7/1976 | Loiacono | 128/349 R |
| 4,585,438 | 4/1986 | Makler . | |
| 5,195,964 | 3/1993 | Kletzky et al. . | |
| 5,370,656 | 12/1994 | Shevel | 606/196 |
| 5,431,637 | 7/1995 | Okada et al. | 604/264 |

*Primary Examiner*—Wynn Wood Coggins
*Assistant Examiner*—Jennifer Maynard
*Attorney, Agent, or Firm*—Patent & Trademark Services; Joseph H. McGlynn

[57] ABSTRACT

A cannula which has a semi-rigid hollow shaft and a soft seal for endocervix to prevent the cannula from slipping out of position during medical procedures, which may be straight, curved or angled at the distal inner end.

11 Claims, 1 Drawing Sheet

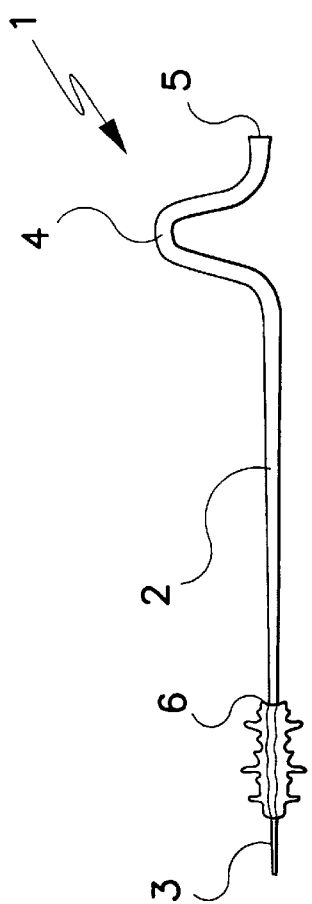
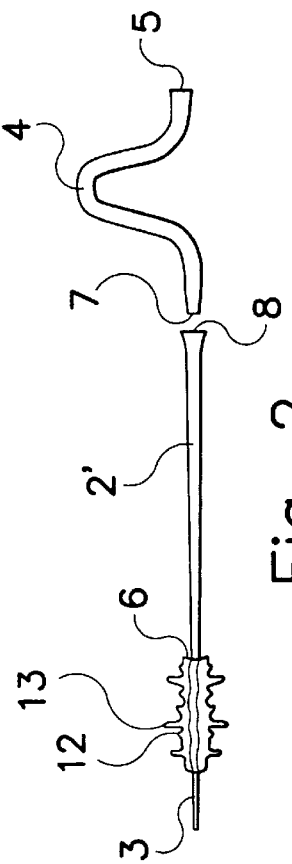
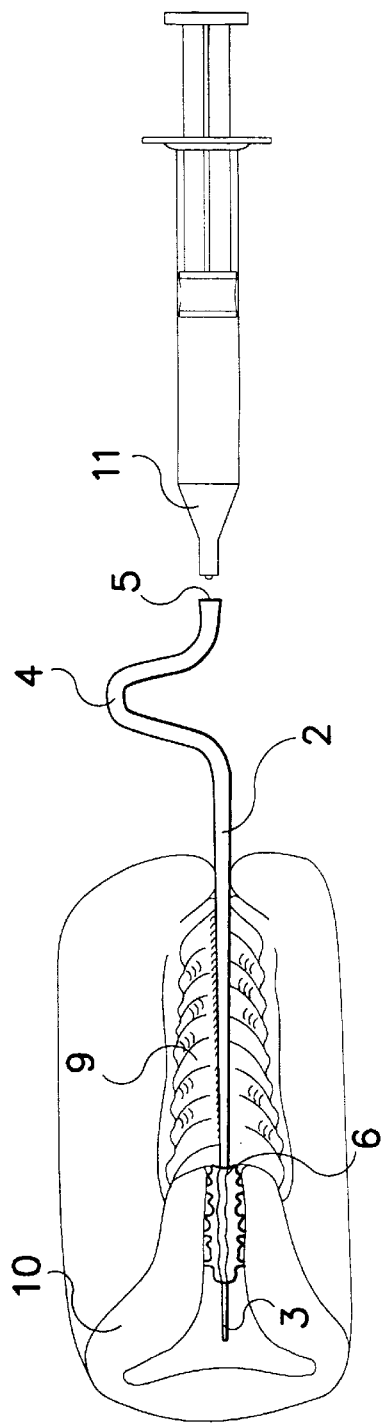

HYSTEROSONOGRAM/ HYSTEROSALPINGOGRAM CANNULA WITH SOFT SEAL

This is a conversion of Provisional application S.N. 60/080,469 filed Apr. 2, 1998.

BACKGROUND OF THE INVENTION

This invention relates, in general, to cannula, and, in particular, to cannula with a soft seal attached thereto.

DESCRIPTION OF THE PRIOR ART

In the prior art various types of cannula have been proposed. For example, U.S. Pat. No. 85.995 to Buffon discloses a syringe with a soft sponge surrounding a rigid shaft to collect waste fluid.

U.S. Pat. No. 3,385,300 to Holter discloses a cervical cannula having a shaft and a tapered cone shaped seal made from a flexible material.

U.S. Pat. No. 3,796,211 to Kohl discloses a biopsy sampler having a shaft surrounded by a cone shaped seal.

U.S. Pat. No. 4,585,438 to Makler discloses an injector with a semi-rigid tubular member surrounded by a seal.

U.S. Pat. No. 5,195,964 to Kletzky et al discloses a cannula with a flexible shaft and a cone shaped seal.

SUMMARY OF THE INVENTION

The present invention is directed to a cannula which has a semi-rigid hollow shaft and a soft seal for endocervix to prevent the cannula from slipping out of position during medical procedures.

It is an object of the present invention to provide a new and improved cannula with a soft seal for endocervix, which will hold the cannula in position during medical procedures.

It is an object of the present invention to provide a new and improved cannula with a semi-rigid shaft to enhance the maneuverability of the cannula.

These and other objects and advantages of the present invention will be fully apparent from the following description, when taken in connection with the annexed drawings.

BRIEF DESCRIPTION OF THE DRAWINGS

FIG. 1 is a side view of the present invention.

FIG. 2 is a side view of another embodiment of the present invention.

FIG. 3 is a side view of the present invention with the cannula in use.

DESCRIPTION OF THE PREFERRED EMBODIMENT

Referring now to the drawings in greater detail, FIG. 1 shows the cannula 1 of the present invention. The cannula has a first end 5 which is cone-shaped in order to receive instruments such as a syringe 11, as shown in FIG. 3. Adjacent to the first end 5 is a flexible looped segment 4 which can be used by the physician to manipulate the instrument during the procedure. Connected to the flexible looped segment 4 is a relatively straight, hollow segment 2. This segment should be made from a material that is semirigid which will allow the physician to more easily manurer the cannula through the vagina 9 and into the cervix 10, as shown in FIG. 3.

The cannula of the prior art make this segment rather flexible, which can make maneuvering the cannula difficult, and due to the flexibility of the prior art cannula, it can kink or bend during insertion. If the cannula is bent, it will be difficult or impossible to insert instruments or medication through the hollow cannula and have the instruments or medication delivered to the desired location. With the semi-rigid nature of the shaft segment 2 the physician can be assured that the cannula 1 will not kink or bend, thereby blocking the internal passage through the cannula for instruments or medication. Also, the semi-rigid nature of the shaft segment 2 will make it easier for the physician to maneuver the cannula as he/she inserts the instrument.

Another problem with the prior art cannula is that the seal or seating member that surrounds the distal end 3 is made from a relatively smooth, hard material. For example, the seal 44 shown in the Kletzky et al reference (U.S. Pat. No. 5,195,964) is made from a semi-rigid silicone rubber or plastic, and, as shown in FIG. 3a of Kletzky et al, the outer surface of the seal is smooth. Generally, the outer surface is made smooth in order to prevent irritation to the patient as the cannula is inserted and/or maneuvered. However this smooth outer surface means that the cannula will not have a strong anchor when placed into position. Manipulation by the physician or an attempt to pass instruments or medication through the hollow cannula, can cause the seal to slip out of position. The alternative solution shown in the prior art has been to make the outer surface of the seals with irregularities such as the teeth 16 shown in the Holter reference (U.S. Pat. No. 3,385,300). While the teeth of Holter will secure the seal more firmly in place, they can also cause irritation to the patient.

The cone-shaped seal 6 of the present invention solves these problems by making the seal 6 from a soft material such as the material used to make sponges. The soft material will prevent irritation to the patient as the physician inserts and manurers the cannula. In addition, the outer surface of the soft material of the seal 6 has a plurality of irregular valleys 12 and lands 13, as shown in FIG. 2, which will allow the seal to contact the inner walls of the opening to the cervix 10 and to firmly, but gently, secure the seal in place. Therefore, when the seal 6 is in position, there will be little, if any irritation to the patient because of the soft material of the seal. In addition, the irregular shaped valleys and lands will assure that the cone-shaped seal is firmly secured in place and will not become dislodged as the physician manurers instruments (not shown) through the hollow cannula, or inserts medication through the cannula by means of the syringe 11.

The embodiment shown in FIG. 2 is essentially the same as the FIG. 1 embodiment except the FIG. 2 embodiment is made in two parts with the shaft 2' separate from the flexible loop segment 4 and the end 5. This will allow the physician to dispose of the shaft 2' after each use, without disposing of the entire cannula. Also, this will make it easier to make the shaft 2' from a different material than the portion containing the flexible loop segment 4. That is the shaft 2' can be made from a semi-rigid material and the portion containing the flexible loop segment 4 can be made from a softer material. Also, the end 8 on the shaft 2' should be made cone-shaped in order to more easily receive the end 7. In all other respects the embodiment shown in FIG. 2 is essentially the same as the FIG. 1 embodiment and works in the same manner.

Although the Hysterosonogram/Hysterosalpingogram Cannula with Soft Seal and the method of using the same according to the present invention has been described in the foregoing specification with considerable details, it is to be understood that modifications may be made to the invention which do not exceed the scope of the appended claims and modified forms of the present invention done by others skilled in the art to which the invention pertains will be considered infringements of this invention when those modified forms fall within the claimed scope of this invention.

What I claim as my invention is:

1. A cervical cannula comprising:

a shaft having a first end and a second end, said first end having means for introducing instruments into an interior of said shaft, said shaft having a loop interposed between said first and second ends, said second end of said shaft having a seal surrounding said shaft adjacent said second end, said seal made from a material that is softer than said shaft, said seal having an irregular surface, and wherein said seal has a plurality of valleys and lands positioned around a periphery of said seal, and wherein said plurality of valleys and lands are irregularly positioned around said periphery.

2. The cervical cannula as claimed in claim 1, wherein said means for introducing instruments into an interior of said shaft is a funnel shaped opening.

3. The cervical cannula as claimed in claim 1, wherein said looped interposed between said first and second ends is made from flexible material.

4. The cervical cannula as claimed in claim 1, wherein said seal is cone shaped with a smaller end of said seal positioned closer to said second end than a larger end of said seal.

5. The cervical cannula as claimed in claim 1, wherein said seal is made from a sponge material.

6. The cervical cannula as claimed in claim 1, wherein some of said valleys are deeper than others of said valleys, and some of said lands are higher than others of said valleys.

7. The cervical cannula as claimed in claim 1, wherein said shaft is made from a semi-rigid materials.

8. The cervical cannula as claimed in claim 1, wherein said loop is made from a flexible material.

9. The cervical cannula as claimed in claim 1, wherein said shaft is made in two parts.

10. The cervical cannula as claimed in claim 7, wherein one of said two parts of said shaft has an end that is smaller than an end on another of said two parts.

11. The cervical cannula as claimed in claim 8, wherein said end that is smaller is cone-shaped.

* * * * *